US009481800B2

(12) United States Patent
Palza Cordero et al.

(10) Patent No.: US 9,481,800 B2
(45) Date of Patent: Nov. 1, 2016

(54) POLYMERIC MATERIALS WITH ANTIFOULING, BIOCIDAL, ANTIVIRAL AND ANTIMICROBIAL PROPERTIES; ELABORATION METHOD AND ITS USES

(71) Applicant: UNIVERSIDAD DE CHILE, Santiago (CL)

(72) Inventors: Humberto Cristian Palza Cordero, Santiago (CL); Raul Quijada Abarca, Santiago (CL); Katherine Delgado Vargas, Santiago (CL); Ivette Pinochet Troncoso, Santiago (CL)

(73) Assignee: UNIVERSIDAD DE CHILE, Santiago (CL)

( * ) Notice: Subject to any disclaimer, the term of this patent is extended or adjusted under 35 U.S.C. 154(b) by 0 days.

(21) Appl. No.: 14/422,054

(22) PCT Filed: Aug. 21, 2013

(86) PCT No.: PCT/IB2013/056768
§ 371 (c)(1),
(2) Date: Feb. 17, 2015

(87) PCT Pub. No.: WO2014/030123
PCT Pub. Date: Feb. 27, 2014

(65) Prior Publication Data
US 2015/0218390 A1    Aug. 6, 2015

(30) Foreign Application Priority Data

Aug. 24, 2012 (CL) .................................. 2350-2012

(51) Int. Cl.
*C09D 5/14* (2006.01)
*C08K 3/08* (2006.01)
(Continued)

(52) U.S. Cl.
CPC ............. *C09D 5/1637* (2013.01); *A01N 25/10* (2013.01); *A01N 25/34* (2013.01); *A01N 59/20* (2013.01);
(Continued)

(58) Field of Classification Search
None
See application file for complete search history.

(56) References Cited

U.S. PATENT DOCUMENTS 4,769,268 A     9/1988   Burton
4,975,327 A  *  12/1990  Somasiri ................. C23C 14/20
                                                    148/276
(Continued)

FOREIGN PATENT DOCUMENTS

JP      A-07-048744       2/1995
JP      A-08-143740       6/1996
(Continued)

OTHER PUBLICATIONS

International Search Report for corresponding International Patent Application No. PCT/IB2013/056768 (mailed Mar. 6, 2014).
(Continued)

*Primary Examiner* — Peter A Salamon
(74) *Attorney, Agent, or Firm* — Merchant & Gould P.C.

(57) ABSTRACT

The present invention is related to polymeric materials, in particular thermoplastic or resins, with antifouling, biocidal, antiviral and antimicrobial properties. In particular, the present invention comprises a polymeric material with antimicrobial properties, wherein said antimicrobial property is given by the controlled and maintained in time release of elements or compounds with antimicrobial properties. The present invention also relates to the preparation method and products generated from said polymeric materials with antimicrobial properties.

9 Claims, 4 Drawing Sheets

(51) Int. Cl.
  C08K 3/22    (2006.01)
  C09D 5/16    (2006.01)
  A01N 25/10   (2006.01)
  A01N 25/34   (2006.01)
  A01N 59/20   (2006.01)
  C09D 7/12    (2006.01)
  C08J 3/22    (2006.01)

(52) U.S. Cl.
  CPC .. *C08J 3/22* (2013.01); *C08K 3/08* (2013.01); *C09D 5/14* (2013.01); *C09D 5/1662* (2013.01); *C09D 7/1275* (2013.01); *C08J 2323/12* (2013.01); *C08K 2003/085* (2013.01)

(56) References Cited

U.S. PATENT DOCUMENTS

| | | | |
|---|---|---|---|
| 2004/0247653 A1* | 12/2004 | Gabbay | A01N 57/20 424/443 |
| 2005/0100574 A1 | 5/2005 | Furukawa et al. | |
| 2008/0171068 A1 | 7/2008 | Wyner et al. | |
| 2008/0193496 A1* | 8/2008 | Gabbay | A01N 59/20 424/404 |
| 2011/0200674 A1 | 8/2011 | MacKay | |
| 2012/0294919 A1 | 11/2012 | Jaynes et al. | |

FOREIGN PATENT DOCUMENTS

| | | |
|---|---|---|
| JP | A-11-043612 | 2/1999 |
| WO | WO 2006/100665 | 9/2006 |
| WO | 2008/122131 A1 | 10/2008 |
| WO | 2012/127326 A1 | 9/2012 |
| WO | 2015/011630 A1 | 1/2015 |

OTHER PUBLICATIONS

Delgado et al. "Polypropylene with embedded copper metal or copper oxide nanoparticles as a novel plastic antimicrobial agent." *Letter in Applied Microbiology.* 53:50-54 (2011).

Kim et al. "The effect of types of maleic anhydride-grafted polypropylene (MAPP) on the interfacial adhesion properties of bio-flour-filled polypropylene composites." *Composites: Part A* 38:1473-1482 (2007).

Palza et al. "Toward Tailor-Made Biocide Materials Based on Poly(propylene)/Copper Nanoparticles." *Macromol. Rapid Commun.* 31:563-567 (2010).

Extended European Search Report for EP 13830250.0, mailed Jan. 20, 2016.

\* cited by examiner

POLYMERIC MATERIALS WITH ANTIFOULING, BIOCIDAL, ANTIVIRAL AND ANTIMICROBIAL PROPERTIES; ELABORATION METHOD AND ITS USES

This application is a U.S. National Stage Application under 35 U.S.C. §371 of International Patent Application No. PCT/IB2013/056768 filed 21 Aug. 2013, which claims the benefit of priority to Chile Patent Application No. 2350-2012 filed 24 Aug. 2012, the disclosures of all of which are hereby incorporated by reference in their entireties. The International Application was published in English on 27 Feb. 2014 as WO 2014/030123.

The present invention is related to polymeric materials, more particularly thermoplastic materials or resins, with antifouling, biocide, antiviral and antimicrobial properties. In particular, the present invention comprises a polymeric material with antimicrobial properties, wherein the antimicrobial activity is given by a controlled release, very high during the first periods of contact, and maintained in time of elements or inorganic compounds with antimicrobial properties. The present invention is also related to a preparation method and products generated from said polymeric materials.

FIELD OF THE INVENTION

The present invention is related to polymeric materials, in particular thermoplastic and thermostable materials, also organic coatings of painting type, with biocidal or antimicrobial properties, which can be used as a polymeric master batch (PMB), for its further addition to previously mentioned resins or in direct mix with thermoplastic resin, in particular for fabrication of threads or fabrics with biocidal properties, or in the fabrication of plastics and/or resins with biocidal or antifouling properties.

BACKGROUND

In the market, there is a high demand for plastic materials not only complying with structural and processability requirements which are characteristic of polymers as raw materials, but also to be able to solve further specific and engineering problems. In this context, during the last years a great demand for plastic materials having the property of inhibiting adherence of microorganisms (antifouling) or being antimicrobial has been generated, in such a manner that they can be used in applications so varied such as materials subjected to water flows inhibiting adherence of algae or microorganisms, as well as on fabric or air filters surfaces which require controlling the growth of microorganisms on those surfaces. The latter is more relevant if thermoplastic polymers are addressed, in particular those based on polyolefins (polyethylene or polypropylene), since those represent over 50% of current plastic market, as well as other thermoplastics.

The present invention describes a technology which allows to incorporate structures based on nanoparticles of an element or inorganic compound of specific characteristics, in particular biocidal, to a resin of a thermoplastic and/or thermostable polymer, also to organic coatings such as paintings, resulting in a plastic material which can release ions of said element or inorganic compound in a controlled manner, at a high release rate during the first periods of time, and also maintaining said release rate for long periods of time, maintaining the main features of the resin. This ability to release ions of the new material results in a biocidal plastic, i.e., antimicrobial and/or antiadherent (Antifouling), highly bioactive and long lasting. Thanks to the property of the material of the present invention regarding the high release rate in short times (First days), and due to the control in the release of ions in long term, and also the control of dispersion of the inorganic compound in the polymeric resin, this product overcomes the limitations of other equivalent technologies currently available (metallic alloys based in copper and/or paintings with copper), in particular those related with environmental and processing impact.

The present invention can be used with any polymeric organic resin, as previously described, but thermoplastics are preferred, and in particular polyolefins (polyethylene and polypropylene), wherein the latter represent more than 50% of all commodity plastics, being the most consumed plastic materials currently. Nevertheless, plastic resins are inert to microorganisms, which allows that certain applications during its performance are reduced due to microorganism accumulation, limiting its lifetime, or that in certain applications said resins do not help to avoid propagation of diseases associated to microorganisms. The present invention solves this limitation by incorporating a biocidal or antifouling property to the resin, in order to control distribution and aggregation of the incorporated filling. Current solutions for this problem are adding a compound that can release an agent in time to a resin or changing the plastic material for a copper alloy, of a much higher cost and quite difficult to process. Most of these solutions present a disadvantage, which is the inability to control the release rate of the agent (specially at short times during the first days) and/or biocidal properties of the material are maintained for only a short time, and also, there is no disclosure regarding a dispersion control in the filling, that is to say, the biocidal agent in the polymeric resin, which decreases the bioactive potential of the resulting material. The present invention allows to produce a thermoplastic and/or thermostable material, besides other organic coating, such as painting type, with a controlled antifouling or biocidal property, which depends on the fabrication method, and of prolonged activity, which is a relevant improvement over other existing solutions such as the case of plastic nets covered with copper based paintings and/or the direct use of metallic nets, which for example in aquaculture industry, as well as other applications as those related to intrahospital infections. These advantages are related to a higher flexibility of the material, better processability, reduction in maintenance processes, less weight and ease of operation. Furthermore, when releasing the biocidal agent at a high rate during initial periods of use (first 10 days), and thanks to the dispersion control of the filling or biocidal agent in the polymeric resin, the material avoids the growth of microorganisms in a more effective way than other solutions. To this is added the improvement of environment since the controlled release of the ion of the element or inorganic biocidal compound. The material of the present invention is elaborated by incorporating particles of a biocidal element or inorganic compound into a resin, in a particular case polypropylene, generating a plastic material which can release in a controlled manner ions of the biocidal element or inorganic compound during long periods of time, maintaining its main properties of processability thanks to the dispersion of the biocidal agent in the polymeric resin. That is to say, the resulting material still is a plastic but the technology applied allows to control the kinetics of ion release in time, which is given by the amount and distribution of the active agent, which generates a flexible material that can be produced according to specific needs for its use. In particular, release of the active agent depends directly on its concentration in the resin, and as example, release rates of 5 µg/ml after 100 days in a concentration of 10% w/w are obtained, which can be doubled if the concentration is increased to 50% w/w. The control of dispersion of the filling or biocidal agent is other feature that allows controlling the release of ions, and in this way, the release of the active agent can be improved in more than 40% by only improving the dispersion of particles by using a pre-treatment. This is a huge advantage compared to other existing alternatives, for its flexibility, allowing to comply with potential toxicity norms and processability. Furthermore, by initially releasing ions at a high rate, this material would effectively avoid proliferation of microorganisms during its first initial adhesion stage to the surface thereof.

This new material can be used in all applications where avoiding adherence or growth of microorganisms is needed, such as in aquaculture industry, hospital establishment surfaces, gutter drains, food processing industry, up to common daily massive use articles, such as cell phone housings, door handles, and in general, any surface which is required to maintain a suitable control of microorganism growth.

Thus, this material has a broad market and is worth noting that in Chile, only in 2007 nearly 400 thousand metric tons of polyolefins were processed, from a total of 700 thousand metric tons of plastics. Of many of potential applications of this new product (for example, aquaculture apparatuses, hospital, food industry, packing, etc), the material of the invention is particularly suitable for fabrication of antifouling nets, such as for example in the use of aquaculture, as well as in the fabrication of plastic materials to be used in hospitals, clinics or other applications where the growth and presence of microorganisms is to be controlled. Using as an example the development of salmon industry in Chile, the second worldwide salmon producer, and with no intention of limiting the scope of the present invention, whose uses are very broad, as previously noted, the potential use of the material of the present invention will be explained. In particular, and only as a way of exemplifying one of the many applications that the polymer with biocidal, antifouling activity, of the present invention, and with no intention of limiting the scope of the invention to this particular application, the use of the resin (polymer with biocidal activity) will be described in the fabrication of a net for salmon farming, using a antimicrobial plastic avoiding the fouling phenomena.

Chile has approximately 4 thousand cage systems for aquaculture. It has been reported that one of the most relevant problems of these systems is due to the presence of biological fouling, generating over 45 million US dollar increase in costs yearly. Thus, the use of the material of the present invention limits this issue, producing a direct increase in profit of salmon industry. Also, it is known that worldwide, aquaculture is growing between 7% and 8% yearly. Along with this, and in particular in the case of Chilean salmon industry, which only has 196 operative farming centers of a total of 400, thus Chile has a potential margin of even higher growth, since it already has suitable installations. Again, it is emphasized that the example of salmon industry is only provided as an exemplification of one of many applications that the material of the present invention can have, therefore, the present invention also encompasses other applications wherein the antimicrobial polyolefins, or thermoplastics in general, would have high demand generating a direct benefit to those firms, product of this technology. One of the advantages of the present invention is the control of release of ions, making the material a highly flexible design material, which allows complying with specific requirements and different environmental norms. This is a clear advantage over copper nets or paintings including copper currently available for the salmon industry, besides being economical.

PRIOR ART

The closest document to the present invention corresponds to the international publication WO 2006/100665, corresponding to a polymeric master batch, production processes and products generated from said batch. This publication describes a material with antimicrobial properties wherein the resins can be thermoplastics, and the inorganic agent with antimicrobial properties added is cupric oxide or cuprous oxide microparticles from 0.2 to 20 micrometers. In particular, the process and material require addition of dispersing waxes and other agents, such as chelating agents or metal deactivators. Also, the generated product in said document requires that at least one portion of the microparticles is exposed to the exterior and protrudes from the surfaces of the material. Unlike the above, the present invention uses in particular nanoparticles of an inorganic antimicrobial agent, particularly metallic copper, with sizes from 4 to 500 nanometers (0.010 to 0.5 micrometers), more preferentially between 10 and 80 nanometers, which are completely embedded in the resin forming secondary structures and wherein the surface of the material does not have exposition of the nanoparticles and even less those nanoparticles do not protrude from the surface of the material. Moreover, the method of the present invention, unlike the teachings of WO 2006/100665, does not require the use of dispersion waxes. By using nanoparticles of 4 to 500 nanometers, more preferentially between 10 and 80 nanometers, allows a high ion release rate at short initial times (first 10 days), unlike what happens with microparticles, where no difference can be appreciated between short or long time (FIG. 5). This makes the material of the present invention more effective in applications where avoiding propagation of microorganisms once they are adhered to the surface is needed, and from the first moment in which the material is installed or as soon as the material is begun to use and enters in contact with microorganisms, with no delay, which can be of up to 10 days.

US2005100574 describes a polyester thermoplastic material with an inorganic antibacterial agent, with particle sizes from around 3 micrometers (300 nanometers). Conversely, the present invention considers inorganic antibacterial agent sizes in the range of nanoparticles between 4 to 500 nanometers, more preferentially from 10 to 80 nanometers, which can form secondary structures wherein the resin goes beyond polyester, with the advantages previously described with respect to the ion release control.

JP11043612 describes an antimicrobial resin, resistant to fungi, formed from a thermoplastic and inorganic antimicrobial agents, wherein the particles of said antimicrobial agent have average sizes of 50 micrometers. The present invention uses nanoparticles with sizes from 4 to 500 nanometers, more preferentially from 10 to 80 nanometers, with the advantages previously described with respect to ion release control.

JP8143740 describes an antibacterial resin for extrusion ends, wherein the material with antibacterial properties is antibacterial zeolite. In the case of the present invention, metallic copper, cuprous oxide or cupric oxide nanoparticles are used.

JP7048744 describes filaments of a thermoplastic polymer with antifouling properties or microorganism anti-adherence properties, wherein the filaments are coated with copper compounds, i.e., the copper is present in the surface of the thermoplastic material. The present invention, conversely, uses copper nanoparticles and avoids the presence of said particles on the surface of the thermoplastic material, which grants a better control over the release during longer times.

U.S. Pat. No. 4,769,268 describes thermoplastic compositions to which a stabilized antimicrobial agent is added. In particular, the antimicrobial agent can be organic conjugates with other inorganic agents. The present invention, conversely, uses nanoparticles of inorganic agents, in particular metallic copper, cupric oxide and/or cuprous oxide.

In the scientific publication H. Palza, S. Gutiérrez, K. Delgado, O. Salazar, V. Fuenzalida, J. Avila, G. Figueroa, R. Quijada. Macromolecular Rapid Communications 31: 563-567, 2010, antimicrobial properties of mixtures of polypropylene with 5 nm copper nanoparticles is discussed, wherein the biocidal property, not the release rate, depends on the amount of copper in the thermoplastic resin. Nevertheless, when presenting a high agglomeration, no controlled release of ions is achieved in these samples and there is no evidence on the dependence of the amount of nanoparticles. No report is made either for short term release, which is an improvement of the present invention when using nanoparticles between 4 and 300 nanometers, more preferentially between 10 and 80 nanometers.

In the scientific publication K. Delgado, R. Quijada, R. Palma, H. Palza. Letters in Applied Microbiology. 53; 50-54, 2011, copper oxide nanoparticles are used, which are added directly to the polymeric resin with no prior treatment and without using any kind of master-batch or concentrate, which is traduced in a low release rate compared to the present invention, wherein the use of prior treatment of the particles improves the dispersion in terms of secondary structures formed by the nanoparticles. This improvement makes that increases of over 50% in the release rate of the active agent can be reached.

It is worth noting that in the present invention, when reference to properties or antimicrobial qualities is made, is to be understood that those are equivalent to properties or biocidal qualitis, and therefore, it can be extended to anti adherent properties (antifouling).

BRIEF DESCRIPTION OF THE INVENTION

The present invention corresponds to a polymeric material, preferentially thermoplastic, thermostable and/or organic coatings painting type, with antimicrobial properties. Said antimicrobial properties are given by the controlled addition of nanoparticles of elements or inorganic compounds with biocidal qualities. Preferentially, the polymeric material corresponds to polyolefins, and the inorganic element corresponds to metallic copper nanoparticles or cupric oxide or cuprous oxide nanoparticles, or combinations thereof, which are treated prior to its incorporation into the polymeric resin and wherein said nanoparticles are well dispersed in the resin and form secondary structures inside the resin.

DEFINITIONS

Figure 1:
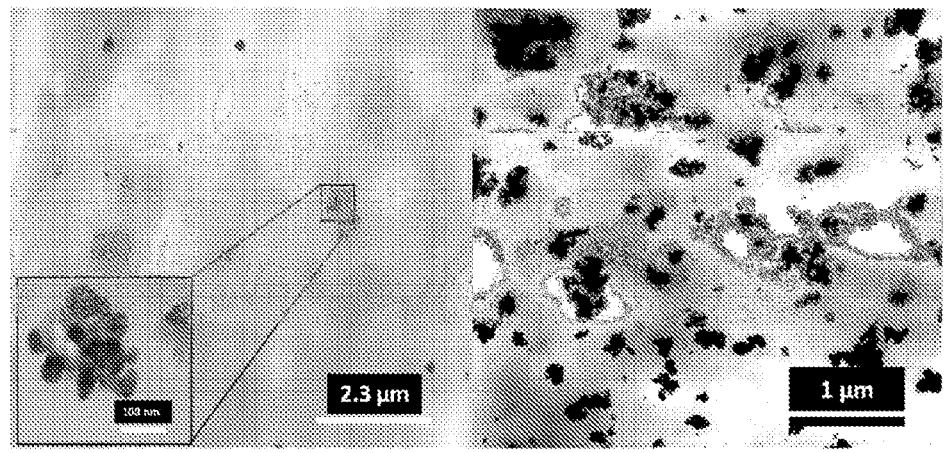
FIG. 1: Representative microphotograph taken from an transmission electron microscope (TEM) of a typical biocidal composite material. This image shows how the nanoparticles form secondary structures of micrometric order.

In the present document, when reference is made to a resin, this term includes polymeric resins, plastics, thermoplastics, organic polymeric resins, such as thermoplastic resins, thermostable resins, and also encompasses organic coatings of painting type.

In the present document, when the material of the invention is mentioned, this is a resin or thermoplastic or a polymer with biocidal, anti-adherent, antimicrobial properties, is referred to the properties of an agent allowing the elimination of microorganisms (bactericidal action) or inhibits its growth (bacteriostatic action). In case of the anti-adherent property, this is referred to the property that the material of the present invention acquires to avoid adherence of microorganisms to form a biofilm and/or kill the microorganisms already adhered inhibiting their growth, producing the so called bio fouling or fouling (antifouling action).

In the present document, the term pre-treatment, is referred to different processes to which nanoparticles with biocidal properties can be subjected before incorporating them to the final resin. There are many pre-treatment options, such as dissolving nanoparticles in an organic solvent; using a compatibilizer, such as for example maleic anhydride; preparing a master-batch in a resin which can be different or the same resin of the final product; functionalize the surfaces of the nanoparticles with surfactant agents; among other options.

DETAILED DESCRIPTION OF THE INVENTION

The present invention consists of a material with antimicrobial properties, a method for its elaboration and the products than can be fabricated based on said material with antimicrobial properties.

In particular, the material corresponds to a polymeric resin: thermoplastic, thermostable or organic coating of paintings type, to which pre-treated nanoparticles between 4 and 500 nanometers are added, preferentially from 10 to 80 nanometers, of an element or inorganic compound with antimicrobial qualities, wherein the nanoparticles form secondary structures, as aggregates, which can have size from 0.1 to 100 micrometers, and wherein said secondary structure is embedded in the thermoplastic resin, in such a manner that said nanoparticles are not present on the surface of the material. These nanometric features, together with the type of dispersion of the biocidal agent achieved, allows a prolonged, elevated and controlled release of ions of the material with antimicrobial qualities. This dispersion and morphology of the particles helps to control the release from the nanoparticles producing that the total release is higher and said release rate is higher in short times. This feature of high release in short times avoids initial settlement of microorganisms which inhibits formation of more complex biofilms, in general composed by exopolysaccharides, and highly resistant to antimicrobial agents. This effect is not observed with traditional micrometric particles.

Nanoparticles are present between 1% in weight up to 80% in weight with respect to the polymeric resin.

More particularly, the polymeric resin avoids the release of whole nanoparticles, which is assured by the formation of secondary structures, and only allows the controlled release of ions of the element or inorganic compound with antimicrobial qualities, avoiding release of whole particles to the environment, a phenomena known as leaching. Therefore, the material of the present invention does not represent a threat due to acute toxicity since the release of ions is made at a determined rate, prolonged in time which can be adjusted depending on the element or inorganic compound ratios with respect to the thermoplastic material. Also, potential toxicity is avoided since the nanoparticle is in the bulk of the material and is not detached from the polymeric resin. Also, by having an homogeneous distribution of secondary structures, a higher release of the active agent is achieved, turning it more effective than other solutions.

In particular, the material of the present invention has the advantage of lacking inorganic antimicrobial agent particles on the surface thereof. More particularly, and with the end of exemplifying the invention, but with no intention on limiting its scope, in the case of a polypropylene resin said particles are not detected on the surface of the material using a x-ray photoelectron spectroscopy (XPS).

In a particular embodiment, the resin is selected among thermoplastic resins which are selected among: polyolefins (polypropylene, polyethylene) and its copolymer derivatives and mixtures thereof; polyester; polyamides; polyestirene; aromatic polyamides; polycarbonates; polyamides (nylon); polyurethane; polyvinyl chloride (PVC); latex based resins; polylactic acids; elastomers (polyisoprene, polybutadiene); polybutadiene copolymers; polyacronitrile; polychloroprene; silicon; vinyl ethylene polyacetate; polyvinyl acetate; epoxy group derived polymers and cyanocrylates among others; and organic coatings of painting type selected among water-based paintings, oil-based paintings, and latex-based paintings.

In other embodiment, nanoparticles of the element or inorganic compound with antimicrobial properties is selected among metallic copper, cupric oxide or cuprous oxide, or other compounds that can release copper ions, as well as silver or zinc ions, or combinations thereof.

Furthermore, the materials according to the present invention can include nanoparticles with antimicrobial or biocidal properties with sizes between 100 and 800 nanometers, and mixtures of different biocidal particles among the limits established in this patent. Nanoparticles with antimicrobial or biocidal properties, are pre-treated in order to control its dispersion in the final polymeric resin. For example, and with no intention of limiting the scope of the invention, among the mentioned pre-treatments are included:

Using a compatibilizer agent to prepare a master-batch (typically polypropylene grafted with maleic anhydride or the same resin of the final product but with a higher molecular weight). In this case, the master-batch is diluted in the final resin.

Dissolving nanoparticles with antibacterial or biocidal properties in organic/inorganic solvents using mechanical stirring and/or ultrasound. In this case, the liquid mixture is added to the melted resin.

Using a concentrated pre-mix of nanoparticles with antibacterial or biocidal properties in the same final resin in order to double shear forces that particles suffer and thus improve dispersion.

Performing a superficial functionalization of nanoparticles with surfactant agents, such as for example any thiol derivative, such as hexanethiol, among others.

Other pre-treatment methods are known by experts in the art.

In a particular embodiment, when the material with antimicrobial properties is submerged in a deionized water solution, the ion release rate is in the range from 1 to 20 µg/ml depending on the concentration of the inorganic agent and exposition time. In particular, the ion release rate is related to the ratio, in weight or volume, between nanoparticles with antimicrobial properties and the polymeric resin of thermoplastic material.

It is hypotetized that the antimicrobial effect of the material of the present invention is produced by ion diffusion of the element or inorganic compound from the bulk of the material to the exterior due to water molecule diffusion from the exterior to the interior of the material through the amorphous region of the polymer.

Figure 2:
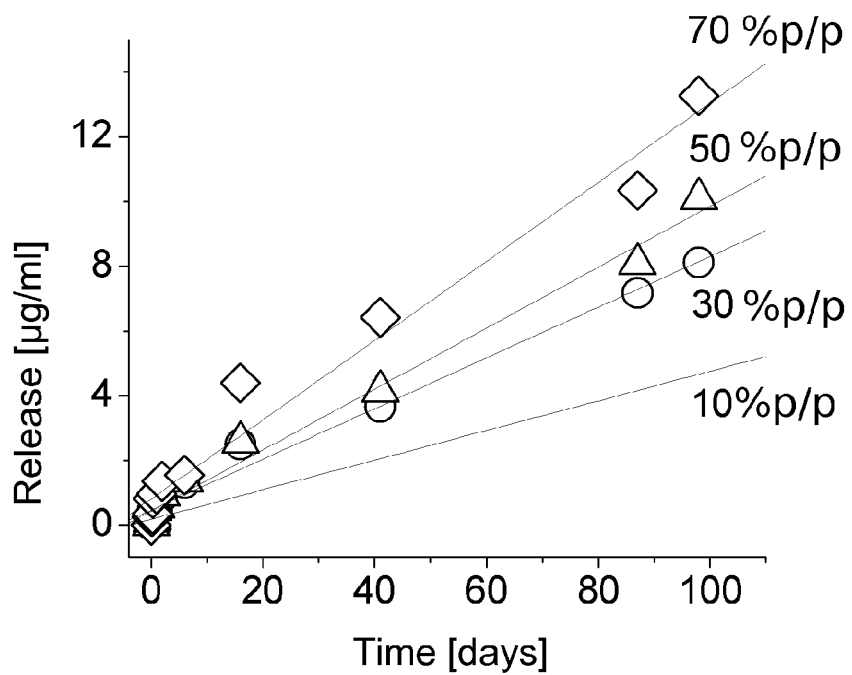
FIG. 2: Plot showing the release of copper ions, for different increasing ratios of copper nanoparticles/resin (PP) in function of time.
Figure 3:
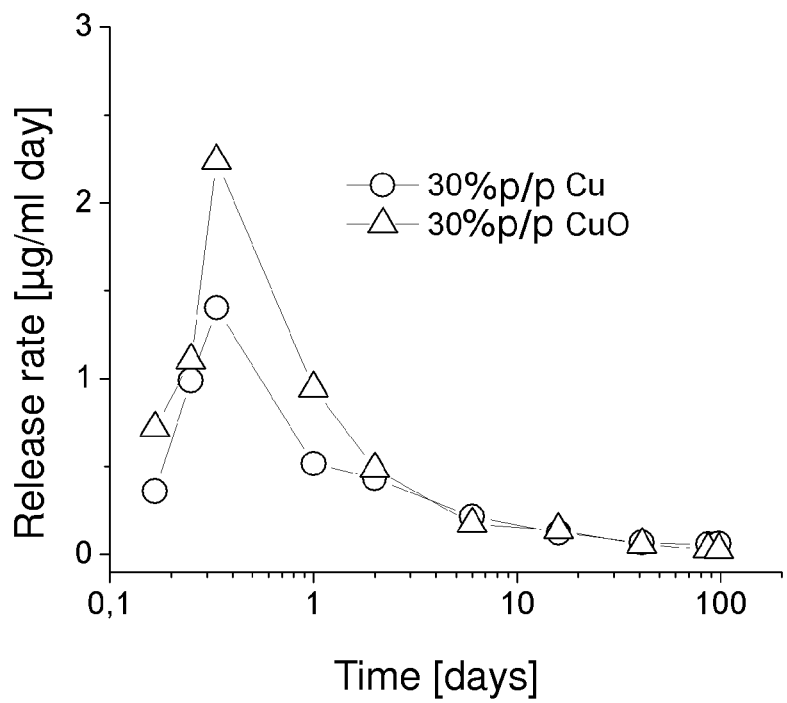
FIG. 3. Plot showing the copper ion release rate, showing that these nanoparticles are able to release at a higher rate at short times.
Figure 5:
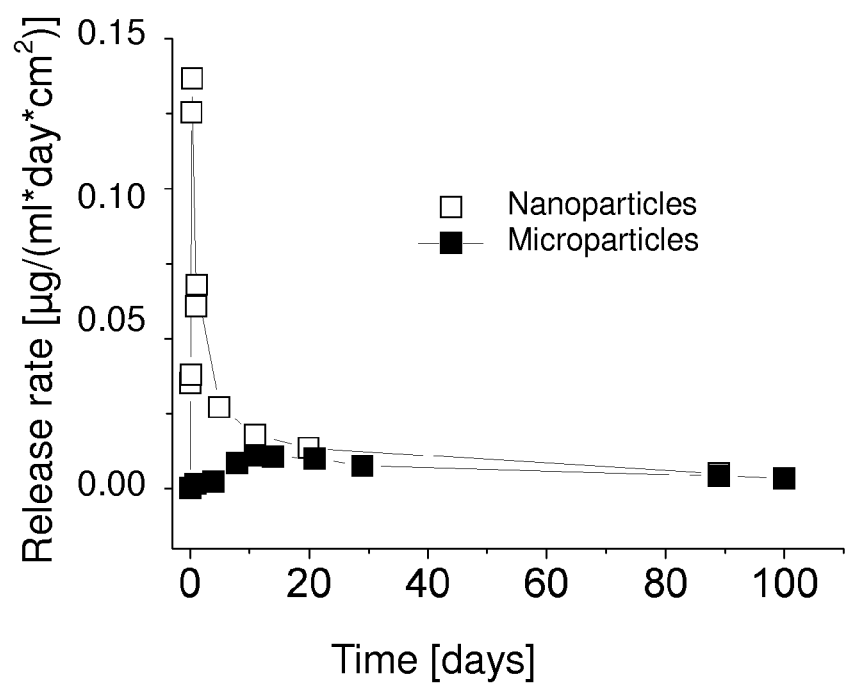
FIG. 5: Plot showing the high copper ion release rate from the plastic material based on copper nanoparticles compared to one based in microparticles.
Figure 6:
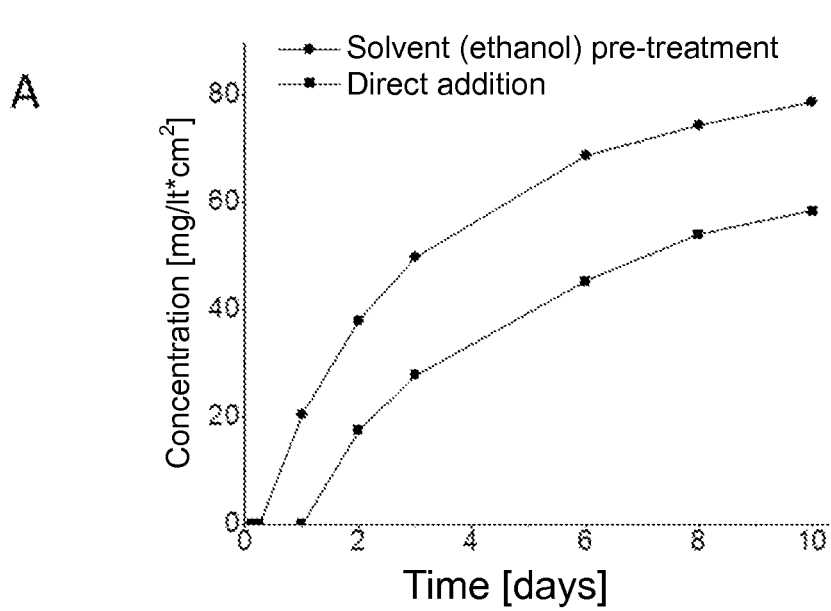
FIG. 6: Plots showing the difference in release rates when using the pre-treatment method to the nanoparticles, according to the present invention, compared to resins prepared with no pre-treatment of nanoparticles, wherein A) pre-treatment using a solvent (ethanol) and B) pre-treatment is incorporation of nanoparticles in a master-batch, prior to the final resin preparation.
Figure 6:
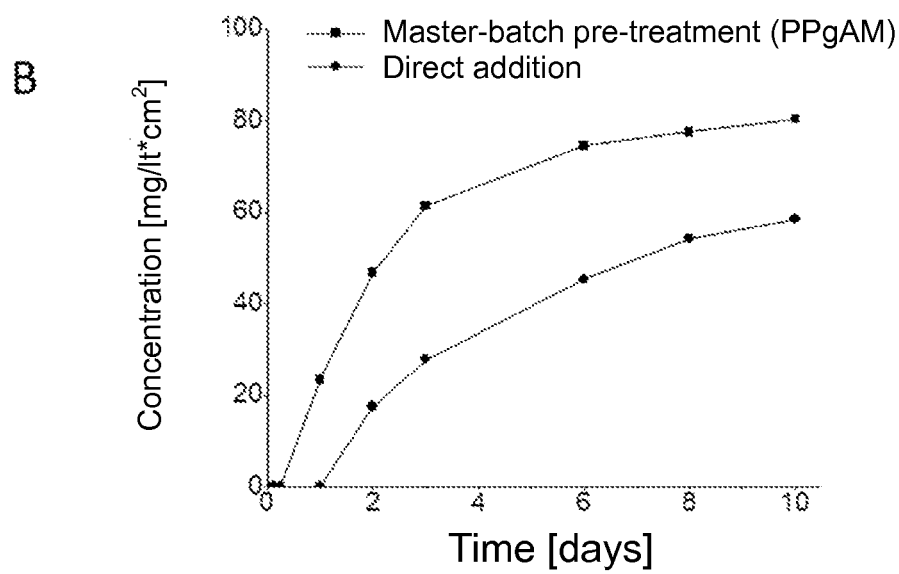

In order to exemplify the latter, and with no intention on limiting the scope of the present invention, the copper ions release rate in a polypropylene resin is observed in FIG. 2. FIG. 3 shows that these particles, having sizes between 4 and 500 nanometers, more preferentially between 10 and 80 nanometers, a high release rate is observed at short times (first 10 days), which is improved compared to other types of biocidal agents in thermoplastic matrices. On the other hand, FIG. 5 shows that this high release rate is only observed for nanometric particles since micrometric particles have no significant changes during release during all the measuring time. It is also observed that for longer times, higher than 50 days, the release rates of the material fabricated with nanoparticles is equivalent to release rates fabricated with microparticles. FIG. 6 shows that pre-treating the particles in an organic solvent (FIG. 6A) and using a pre-treatment wherein nanoparticles are incorporated in a master-batch prior to their incorporation in the final polymeric resin (FIG. 6B), achieves to increase the total release of the active antimicrobial agent. Similar results are achieved using other pre-treatments as the ones previously disclosed.

The present invention further considers the method for elaboration of the polymeric resin with antimicrobial and biocidal properties, wherein said method comprises the following steps for the particular case of thermoplastic resins, although with no limitation to this example:

A. Melt a suitable amount of thermoplastic at a proper temperature, generally between 20 or 30° C. higher than the fusion temperature of the material or 20 or 80° C. higher than the vitreous transition temperature for amorphous materials. In general, the processing temperature of the thermoplastic material is used. For example, in case of polypropylene the temperature is between 170 and 220° C.

B. In a controlled atmosphere with no oxygen, such as for example a nitrogen atmosphere or other noble gas atmosphere, such as argon, or even under vacuum, depending on the application, the melted thermoplastic is stirred at a speed between 20 to 400 rpm, depending on the equipment and properties of the resin.

C. In parallel, a pre-treatment of the nanoparticles with antibacterial or biocidal properties of size between 4 and 80 nanometers, more preferentially between 10 and 80 nanometers, is required, in order to achieve a proper dispersion thereof in the resin. The pre-treatment can correspond to:
  I. A mix (master-batch or concentrate) of nanoparticles with a compatibilizer agent (for example between 10 to 70% w/w of polypropylene grafted with maleic anhydride and between 90 to 30% w/w of biocidal material)
  II. Dissolving the nanoparticles with antibacterial or biocidal properties in organic or inorganic solvents with mechanical stirring and/or ultrasound.
  III. Preparing a mixture of nanoparticles in a polymeric resin which can be different or the same resin of the final product in order to increase shear forces the particles are subjected to, thus improving dispersion.
  IV. Functionalize nanoparticles with organic type surfactants, preferentially thiolated compounds, such as for example hexanethiol.

D. Stir continuously the thermoplastic melted in step B), adding to the melted thermoplastic the pre-treated nanoparticles, in order to achieve a ration from 1% w/w to 80% w/w of 4 to 80 nanometer nanoparticles, more preferentially from 10 to 80 nanometers, of an element or inorganic compound with antimicrobial properties E. Keep stirring for 5 to 30 minutes depending on the properties of the thermoplastic resin;

F. Cool down and recovery of the produced thermoplastic material.

In the case that other type of resin is used, the elaboration method consist in mixing pre-treated nanoparticles with the pre-polymer prior to a curing stage, or directly to a resin dissolved in a proper solvent, according to the processing method corresponding to the final resin. The following describes the method for the case of thermostable resins and/or organic coatings of painting type:

Pre-treating nanoparticles with antibacterial or biocidal properties of a size between 4 to 500 nanometers, more preferentially between 10 to 80 nanometers, in order to have a proper dispersion in the resin, wherein said pre-treatment may be:
  mixing (master-batch or concentrate) of nanoparticles with an organic agent such as for example between 10 to 80% w/w of additives based on the pre-polymer or on monomer or a solvent or other agent added to the resin for its processing and between 80% to 30% w/w of the biocidal material;
  dissolving the nanoparticles with antibacterial or biocidal properties in organic/inorganic solvents using mechanical stirring and/or ultrasound mixing the nanoparticles in the same final polymeric resin in order to increase or double shear forces on the particles and thus improve dispersion;
  functionalizing the surface of nanoparticles with organic agents of surfactant type, wherein the organic agents of surfactant type are thiolated compounds
stir continuously pre-cured thermostable resin and/or organic coatings of painting type and add to the thermostable resin and/or organic coating of painting type pre-treated nanoparticles in order to reach a ratio between 1% w/w to 80% w/w of nanoparticles of 4 to 500 nanometers, more preferentially between 10 to 80 nanometers of an element or inorganic compound with antimicrobial properties.

As previously mentioned, in the process of incorporating nanoparticles to the resin, these are associated forming secondary structures, which are presently called agglomerates. Also, the distribution of agglomerates in a particular resin is improved when compared to a resin prepared without pre-treatment of nanoparticles.

In this manner, the agglomerates, when using the pre-treatment method previously disclosed, reach a size between 0.1 to 60 micrometers, more preferentially from 0.1 to 50 micrometers, more preferentially from 0.1 to 40 micrometers, even more preferentially from 0.1 to 30 micrometers, and even more preferentially from 0.1 to 20 micrometers.

When comparing a resin prepared according to the method of the present invention to a resin prepared with no pre-treatment of nanoparticles, a better distribution of agglomerates is observed in the resin. This is confirmed when observing under optical microscope that the average size of agglomerates decreases, as its distribution is more homogeneous in the resin.

In particular, in order to evaluate this effect in improvement of distribution, an agglomerate dispersion index has been defined, allowing determining a density of agglomerates of nanoparticles.

The agglomerate dispersion index relates to two most important features in terms of dispersion: first the average volume of agglomerates (Vp) and second the average number of agglomerates (Np). Thus, the agglomerate dispersion index Id is defined as:

$$I_d = \frac{N_p}{V_p}$$

wherein Np is a number, Vp is expressed in cubic micrometers, and when the index is higher, the better the nanoparticle agglomerate dispersion is.

To quantify the distribution of agglomerates in the resin, an agglomerate density has been defined, which in the case of the present invention must be higher than 2. Said agglomerate density is defined as 100 times the agglomerate dispersion index (defined as the ration between the average number of agglomerates and the average volume of agglomerates), observed in a predetermined volume, divided by the ratio in weight between nanoparticles of the element or inorganic compound and the thermoplastic and/or thermostable resin and/or organic coating of painting type.

Thus, the agglomerate density of nanoparticles defined as D, corresponds to:

$$D = 100 \cdot \frac{I_d}{V \cdot C}$$

wherein Id is the previously defined agglomerate dispersion index, V is the volume of the evaluated material sample, expressed in cubic millimeters, C is the concentration of biocidal compound in the resin, expressed as weight/weight percentage. Therefore, D has units of number of agglomerates per cubic micrometer, cubic millimeter, biocide percentage in weight.

The increase in the dispersion index, that is to say, smaller agglomerates or higher number of agglomerates, is traduced in an increase in the agglomerate density (D) which has as a consequence that the resin prepared according to the present invention achieves higher release rates of the biocidal or antimicrobial agent, maintained in time, as well as achieving higher release rates at initial times, allowing to exert a biocidal activity from the beginning, with no considerable delay times, as happens in the case of resins prepared with no pre-treatment step.

In a particular embodiment, the material obtained in this way can be used as a polymeric master-batch (Polymeric Master Batch, PMB) which can be melted and mixed with the same polymer or other polymers, thus having a final product with a ratio between 30 to 80% in weight of nanoparticles of an element or inorganic compound with antimicrobial properties.

The material obtained can be used for fabricating varied products elaborated with polymeric materials, and which would be benefited from having an antimicrobial property.

In particular, and only for exemplification ends, and with no intention of limiting the scope of the invention, the material obtained from the previously described processes can be used in manufacturing threads for production of all types of fabrics and nets, and therefore, for fabrication of garments, masks, bedclothes, pillows and other household articles, it can also be used in elaboration of laminated, extruded, molded, injected plastic products, or products that can be produced by any other industrial mean.

Other field of application of the material of the present invention are containers, coating surfaces for tables, shower curtains, cleaning tools, crystals, shoes, disposable slipsoles, intra-hospital use materials, door handles, window frames, air filters, nets or cages for aquaculture industry, etc.

EXAMPLES

Example 1

Preparation of a Polypropylene Resin with Metallic Copper Nanoparticles

Different polypropylene materials were prepared with metallic copper nanoparticles in different ratios.

A Brabender plasticorder mixer was used at 190° C., using stirring at 110 rpm for 10 minutes, in a controlled nitrogen atmosphere to avoid oxidative degradation during the process. During the stirring period, different amounts of copper nanoparticles, of average size 10 nanometers were added. The ratios of copper nanoparticles and thermoplastic material in the different materials were 0% (control) 1%, 5%, 10% and 20% w/w.

In particular, for example, the agglomerate density (D) for the resin of 5% w/w was 0.42 m since the average agglomerate number was 140 units, with an average volume of agglomerates of 268,000 cubic micrometers. The samples used for determination of these indexes were laminates of 0.1 mm thick, and a surface of 0.25 mm$^2$ was analyzed, i.e., a volume of 0.025 mm$^3$. At least 12 different zones were tested from three different films per sample in order to collect representative values in the measurements.

Example 2

Preparation of a Polypropylene Resin with Metallic Copper Nanoparticles, which were Pre-Treated Using an Organic Solvent Similarly to Example 1, different polypropylene materials were prepared with metallic copper nanoparticles in different ratios, using ethanol as solvent for pre-treatment of the nanoparticles. Nanoparticles, as in the previous example, had a size of 10 nanometers. The amount of nanoparticles in ethanol was determined in order to achieve the following ratios in the final thermoplastic resin: 0% (control) 1%, 5%, 10% y 20% weight/weight.

In this case, the agglomerate density (D) for the case of 5% w/w resin was 5.1. The average number of agglomerates in the sample was 90 units and the average volume of said agglomerates was 14,000 cubic micrometers.

FIG. 6A shows the comparison of the resin prepared according to Example 1 (direct addition) with the pre-treatment made with ethanol (pre-treated with solvent (ethanol)). It is clearly observed an increase in the release rate that is maintained during all the test period, and wherein it is clear that the material prepared with pre-treated nanoparticles shows a high release even during the first hours of the first day, while release of the material prepared with nanoparticles without pre-treatment is only detected from the second day. The increase in the release rate when comparing a material prepared with nanoparticles without pre-treatment to the pre-treated nanoparticles with ethanol, is nearly 56% higher at the end of the test period, and nearly 90% higher at the beginning of the test.

Example 3

Preparation of a Polypropylene Resin with Metallic Copper Nanoparticles, Pre-Treated by Incorporation to a Master-Batch Similarly to example 1, different polypropylene materials were prepared with metallic copper nanoparticles in different ratios, using the incorporation of nanoparticles in a polypropylene master-batch using maleic anhydride as compatibilizer. Nanoparticles were incorporated in a ratio of 5% w/w in the masterbatch. Afterwards, the amount of nanoparticles was determined to reach the following rations in the final thermoplastic resin: 0% (control) 1%, 5%, 10% y 20% volume/volume. Nanoparticles, as well as in previous examples, had a size of 10 nm.

FIG. 6B shows the comparison of the resin prepared in Example 1 (direct addition) to the pre-treatment corresponding to preparation of a master-batch (pre-treatment master-batch (PPgAM)). It is clearly observed an increase in the release rate which is maintained during all the test period, and wherein it is clear that the material prepared with pre-treated nanoparticles shows a high release rate even during the first hours of the first day, while release from the material prepared with nanoparticles without pre-treatment, is only detected from the second day. The increase in release rate when comparing a material elaborated with nanoparticles without pre-treatment to one prepared with nanoparticles pre-treated in a master-batch is nearly 45% higher at the end of the test period and nearly 160% at the beginning of the test.

Example 4

Elaboration of Laminates of Antimicrobial Material

The materials obtained in Example 1 were molded in a press at 190° C. with a 50 bar pression for 5 minutes. The press was cooled down with cold water, resulting in a 1 mm thick film. FIG. 1 shows the dispersion of nanoparticles using transmission electron microscopy (TEM), showing the secondary structure formed by copper nanoparticles in the films obtained in this example. Individual particles are present but given the resolution of the microscope, cannot be detected.

Example 5

Characterization of Antimicrobial Features of the Material

The films obtained in Example 2 were cut in pieces of 20 mm×20 mm and subjected to a bacterial culture, for evaluation of their antimicrobial effect.

*E. coli* bacteria were cultured in Luria broth at 37° C.

Figure 4:
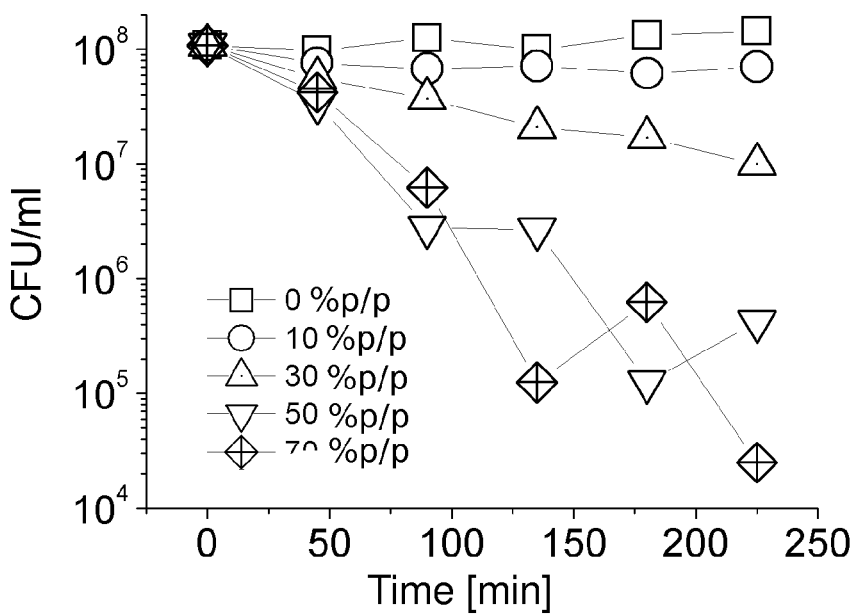
FIG. 4: Plot showing the biocidal effect of the present invention in function of time and the amount of nanoparticles for the particular case of a polypropylene resin.

A 50 ml aliquot from *E. coli* culture, with a concentration of 106 colony forming units (CFU) was deposited, under aseptic conditions, over pieces of the material of the present invention. The pieces of film were covered with glass, and kept for times between 30 to 360 minutes at 37° C. Once the determined time passed, 40 microliter aliquots were taken and grown in agar plates at 37° C. for at least 16 hours to perform a colony count. The result is observed in FIG. 4, wherein the bactericidal effect is observed depending on the ratio of copper nanoparticles embedded in the material.

This figure also shows that the release rate, and in consequence the biocidal power of the final resin, can be controlled depending on the ratio of nanoparticles in the resin. This is also observed in the case of resins prepared with nanoparticles that were pre-treated (FIGS. 6A and 6B), wherein the release rate of the biocidal agent is higher in the case where the resins were elaborated with pre-treated nanoparticles.

We claim:

1. A polymeric material with antimicrobial and/or biocidal properties for making plastic products with antimicrobial, antifouling, and biocidal properties, wherein the polymeric material comprises a thermoplastic and/or thermostable resin and/or organic coating of painting type comprising nanoparticles from 4 to 500 nanometers, of an element or inorganic compound with antimicrobial and biocidal properties, wherein the nanoparticles of the element or inorganic compound with antimicrobial properties are pre-treated to improve final dispersion and are completely embedded in the thermoplastic resin and do not protrude from the surface of the resin, and wherein the nanoparticles of the element or inorganic compound with antimicrobial properties form agglomerates of sizes from 0.1 to 100 micrometers, wherein the ratio in weight between nanoparticles of the element or inorganic compound and the thermoplastic and/or thermostable resin and/or organic coating of painting type is between 1 and 80% in weight, and wherein said agglomerates are homogeneously dispersed in the resin, in order to obtain an agglomerate density greater than 2, wherein said agglomerate density is defined as 100 times the ratio between the average number of agglomerates and the average volume of agglomerates, observed in a determined volume, divided by the ratio in weight of nanoparticles of the element or inorganic compound and the thermoplastic and/or thermostable resin and/or organic coating of painting type.

2. The polymeric material with antimicrobial and/or biocidal properties according to claim 1, wherein the resin is selected from the group consisting of a thermoplastic resin selected from polyolefins and copolymer derivatives and mixtures thereof; polyester; polyamides; polystyrene; aromatic polyamides; polycarbonates; polyamides; polyurethane; polyvinyl chloride (PVC); latex based resins; polylactic acids; elastomers; polybutadiene copolymers; polyacrylonitrile; polychloroprene; silicon; ethylene vinyl polyacetate; polyvinyl acetate; epoxy groups copolymers and cyanoacrylates; or a thermostable resin; and organic coatings of painting type selected from the group consisting of water-based paints, oil-based paints, and latex-based paints.

3. The polymeric material with antimicrobial and/or biocidal properties according to claim 1, wherein the polymeric material further comprises particles of the element or inorganic compound with sizes between 100 and 800 nanometers, and mixtures of biocidal particles of different sizes.

4. The polymeric material with antimicrobial and/or biocidal properties according to claim 1, wherein the inorganic compound with antimicrobial properties is selected from the group consisting of metallic copper, cupric oxide, cuprous oxide, inorganic compounds that can release copper ions, inorganic compounds that can release zinc, silver, metallic silver, and metallic zinc ions.

5. The polymeric material with antimicrobial and/or biocidal properties according to claim 4, wherein the inorganic compound with antimicrobial properties has received a pre-treatment by mixing with compatibilizers or other polymeric and/or organic agents to help with the dispersion in the polymeric resin, wherein the pre-treatment is selected from the group consisting of a mixture with a compatibilizer agent, the same resin of higher molecular weight; by prior dispersion in organic/inorganic solvents selected from the group consisting of water, ethanol, methanol, and acetone; a superficial functionalization of the nanoparticle with organic agents of surfactant type, selected from the group consisting of thiolated compounds.

6. A method for making a polymeric material with antimicrobial and/or biocidal properties comprising a thermoplastic resin according to claim 1, wherein the method comprises the following steps:
   a) melt a suitable amount of a thermoplastic at a temperature between 20 to 30° C. higher than the fusion temperature of the material or 20 to 80° C. higher than the vitreous transition temperature for the case of amorphous materials;
   b) in a controlled atmosphere with no oxygen, a nitrogen atmosphere or other noble gas, or under vacuum, stir the melted thermoplastic at 20 to 400 rpm;
   c) pre-treat nanoparticles with antibacterial or biocidal products with a size between 4 and 500 nanometers in order to have a proper dispersion in the resin, wherein said pre-treatment is selected from:
      i) master-batch or concentrate nanoparticles with a compatibilizer agent and between 90 to 30% w/w of biocidal material;
      ii) dissolve nanoparticles with antibacterial or biocidal properties in organic/inorganic solvents using mechanical treatments and/or ultrasound;
      iii) mix nanoparticles in the same final polymeric resin in order to increase shear forces over the nanoparticles thus improving dispersion; and
      iv) superficial functionalization of nanoparticles with organic surfactant type agents, wherein the organic surfactant type agents are thiolated compounds;
   d) while continuously stirring, add pre-treated nanoparticles in order to reach a ratio between 1% w/w to 80% w/w of nanoparticles between 4 and 500 nanometers of an element or inorganic compound with antimicrobial properties to the melted thermoplastic;
   e) maintain stirring for a period between 5 to 30 minutes; and f) cool down and recover the obtained thermoplastic material.

7. A method for making a polymeric material with antimicrobial and/or biocidal properties of comprising a thermostable resin and/or organic coating of painting type according to claim 1, wherein the method comprises:
   a) pre-treating nanoparticles with antibacterial or biocidal products with a size between 4 and 500 nanometers in order to have a proper dispersion in the resin, wherein said pre-treatment is selected from:
   i) master-batch or concentrate of nanoparticles with a compatibilizer agent and between 90 to 30% w/w of biocidal material;
   ii) dissolving nanoparticles with antibacterial or biocidal properties in organic/inorganic solvents using mechanical treatments and/or ultrasound;
   iii) mixing nanoparticles in the same final polymeric resin in order to increase shear forces over the nanoparticles thus improving dispersion; and
   iv) superficial functionalization of nanoparticles with organic surfactant type agents, wherein the organic surfactant type agents are thiolated compounds;
   b) while continuously stirring the pre-cured thermostable resin and/or organic coatings of painting type, add pre-treated nanoparticles in order to reach a ratio between 1% w/w to 80% w/w of nanoparticles between 4 and 500 nanometers of an element or inorganic compound with antimicrobial properties to the thermostable resins and/or organic coatings of painting type.

8. A process of using a polymeric material with antimicrobial and/or biocidal properties of claim 1, wherein the polymeric material is used as a polymeric master-batch that is mixed with the same base polymer or other polymers for making a material with antimicrobial properties.

9. A process of using a polymeric material with antimicrobial and/or biocidal properties of claim 1, wherein the polymeric material is used for manufacturing threads for production of fabrics and nets; laminated, extruded, molded, or injected plastic products; containers, coating surfaces for tables, shower curtains, cleaning tools, crystals, shoes, disposable slipsoles, intra-hospital use materials, door handles, window frames, air filters, nets or cages for aquaculture industry, and paintings.

* * * * *